(12) United States Patent
Hyde et al.

(10) Patent No.: US 8,385,997 B2
(45) Date of Patent: Feb. 26, 2013

(54) SPECTROSCOPIC DETECTION OF MALARIA VIA THE EYE

(75) Inventors: Roderick A. Hyde, Redmond, WA (US); Nathan P. Myhrvold, Medina, WA (US); Clarence T. Tegreene, Bellevue, WA (US); Lowell L. Wood, Jr., Bellevue, WA (US)

(73) Assignee: Tokitae LLC

( * ) Notice: Subject to any disclaimer, the term of this patent is extended or adjusted under 35 U.S.C. 154(b) by 1454 days.

(21) Appl. No.: 12/001,765

(22) Filed: Dec. 11, 2007

(65) Prior Publication Data

US 2009/0149726 A1 Jun. 11, 2009

(51) Int. Cl.
*A61B 5/1455* (2006.01)
(52) U.S. Cl. ......................... 600/318; 600/310
(58) Field of Classification Search ........... 600/309–344
See application file for complete search history.

(56) References Cited

U.S. PATENT DOCUMENTS

| | | | |
|---|---|---|---|
| 5,123,898 A | 6/1992 | Liboff et al. | |
| 5,224,922 A | 7/1993 | Kurtz | |
| 5,734,498 A | 3/1998 | Krasieva et al. | |
| 6,445,362 B1 | 9/2002 | Tegreene | |
| 6,588,901 B1 | 7/2003 | Grinvald et al. | |
| 6,621,568 B1 | 9/2003 | Yonezawa | |
| 6,721,583 B1 * | 4/2004 | Durkin et al. | 600/318 |
| 6,739,342 B1 | 5/2004 | Fredriksson et al. | |
| 6,961,599 B2 * | 11/2005 | Lambert et al. | 600/318 |
| 7,388,668 B2 | 6/2008 | Potma et al. | |
| 7,461,961 B2 | 12/2008 | Li | |
| 2001/0034478 A1 | 10/2001 | Lambert et al. | |
| 2002/0155630 A1 | 10/2002 | Iwabuchi | |
| 2003/0194589 A1 | 10/2003 | Pratt et al. | |
| 2004/0135998 A1 | 7/2004 | Chin | |
| 2005/0020926 A1 | 1/2005 | Wiklof et al. | |
| 2005/0043636 A1 | 2/2005 | Gaeta et al. | |
| 2005/0087601 A1 | 4/2005 | Gerst, III et al. | |
| 2005/0288564 A1 * | 12/2005 | Iuliano | 600/318 |
| 2006/0012778 A1 | 1/2006 | Vaughnn | |
| 2006/0169314 A1 | 8/2006 | Horio et al. | |
| 2006/0284790 A1 | 12/2006 | Tegreene et al. | |
| 2007/0115461 A1 | 5/2007 | Fairley et al. | |
| 2007/0236785 A1 | 10/2007 | Matsumoto | |
| 2007/0253227 A1 | 11/2007 | James et al. | |
| 2008/0100834 A1 | 5/2008 | Kung et al. | |
| 2008/0297783 A1 | 12/2008 | Urano et al. | |
| 2009/0149726 A1 | 6/2009 | Hyde et al. | |
| 2009/0227044 A1 | 9/2009 | Dosev et al. | |
| 2009/0318784 A1 | 12/2009 | Newman et al. | |
| 2010/0120132 A1 | 5/2010 | Koo | |
| 2010/0196920 A1 | 8/2010 | Lee et al. | |

(Continued)

FOREIGN PATENT DOCUMENTS

WO WO 2008/056171 A2 5/2008
WO WO 2009/009899 A1 1/2009

OTHER PUBLICATIONS

Beare, N.A.V. et al.; "Short Report: Changes in Optic Nerve Head Blood Flow in Children With Cerebral Malaria and Acute Papilloedema"; J. Neurol Neurosurg Phychiatry; 2006; pp. 1288-1290; vol. 77; located at: www.jnnp.com.

(Continued)

*Primary Examiner* — Eric Winakur
*Assistant Examiner* — Marjan Fardanesh

(57) ABSTRACT

Methods, apparatus, and systems for detecting hemozoin and diagnosing malaria infection are disclosed.

31 Claims, 2 Drawing Sheets

U.S. PATENT DOCUMENTS

2010/0222662 A1    9/2010    Hegg et al.
2010/0256467 A1    10/2010    Hegg et al.
2011/0204257 A1    8/2011    Wiseman et al.

OTHER PUBLICATIONS

Caspers, P.J. et al.; "Combined In Vivo Confocal Raman Spectroscopy and Confocal Microscopy of Human Skin"; Biophysical Journal; Jul. 2003; pp. 572-580; vol. 85; Biophysical Society.

Chen, Qijun et al.; "Molecular Aspects of Severe Malaria"; Clinical Microbiology Reviews; Jul. 2000; pp. 439-450; vol. 13, No. 3; American Society for Microbiology.

Cheng, Ji-Xin; Xie, X. Sunney; "Feature Article: Coherent Anti-Stokes Raman Scattering Microscopy: Instrumentation, Theory, and Applications"; Journal of Physical Chemistry B; 2004; pp. 827-840; vol. 108; American Chemical Society.

Egan, Timothy J. et al.; "Haemozoin (β-haematin) Biomineralization Occurs by Self-Assembly Near the Lipid/Water Interface"; FEBS Letters; 2006; pp. 5105-5110; vol. 580; Federation of European Biochemical Societies.

Egan, Timothy J. et al.; "Quinoline Anti-Malarial Drugs Inhibit Spontaneous Formation of β-haematin (Malaria Pigment)"; FEBS Letters; 1994; pp. 54-57; vol. 352; Federation of European Biochemical Societies.

Evans, Conor L. et al.; "Chemical Imaging of Tissue in Vivo with Video-Rate Coherent Anti-Stokes Raman Scattering Microscopy"; PNAS; Nov. 15, 2005; pp. 16807-16812; vol. 102, No. 46; The National Academy of Sciences.

Frosch, Torsten et al.; "In Situ Localization and Structural Analysis of the Malaria Pigment Hemozoin"; Journal of Physical Chemistry B; 2007; pp. 11047-11056; vol. 111; American Chemical Society.

Hammer, Daniel X. et al.; "Adaptive Optics Scanning Laser Ophthalmoscope for Stabilized Retinal Imaging"; Optics Express; Apr. 17, 2006; pp. 3354-3367; vol. 14, No. 8; OSA.

Lieber, Chad A.; Mahadevan-Jansen, Anita; "Development of a Handheld Raman Microspectrometer for Clinical Dermatologic Applications"; Optics Express; Sep. 17, 2007; pp. 11874-11882; vol. 15, No. 19; OSA.

"New Way to Catch Cancer's Spread, Rapid 3-D Retinal Imaging, More at CLEO/QELS 2007"; Medical News Today; Apr. 18, 2007; pp. 1-4; located at: http://www.medicalnewstoday.com/printerfriendlynews.php?newsid=67726.

Romero-Borja, Fernando et al.; "Optical Slicing of Human Retinal Tissue in Vivo With the Adaptive Optics Scanning Laser Ophthalmoscope"; Applied Optics; Jul. 1, 2005; pp. 4032-4040; vol. 44, No. 19; Optical Society of America.

Schoen, C.H.; Dickensheets, D.L.; "Tools for Robotic In Situ Optical Microscopy and Raman Spectroscopy on Mars"; Concepts and Approaches for Mars Exploration; Jul. 2000; p. 275 (printed version 2 pages); located at: http://adsabs.harvard.edu/abs/2000came.work..275S.

Slater, Andrew F.G. et al.; "An Iron-Carboxylate Bond Links the Heme Units of Malaria Pigment"; Biochemistry: Proc. Natl. Acad. Sci. USA; Jan. 1991; pp. 325-329; vol. 88; PNAS.

Tekwani, Babu L.; Walker, Larry A.; "Targeting the Hemozoin Synthesis Pathway for New Antimalarial Drug Discovery: Technologies for In Vitro β-Hematin Formation Assay"; Combinatorial Chemistry & High Throughput Screening; 2005; pp. 63-79; vol. 8, No. 1; Bentham Science Publishers Ltd.

Tripathi, Abhai K. et al.; "Spectrophotometric Determination of De Novo Hemozoin/β-Hematin Formation in an In Vitro Assay"; Analytical Biochemistry; 2004; pp. 85-91; vol. 325; Elsevier Inc.; located at: www.sciencedirect.com or www.elsevier.com/locate/yabio.

Williamson, Tom H. et al.; "Major Review: Color Doppler Ultrasound Imaging of the Eye and Orbit"; Survey of Ophthalmology; Jan./Feb. 1996; pp. 255-267; vol. 40, No. 4; Survey of Ophthalmology.

Wood, Bayden R. et al.; "A Portable Raman Acoustic Levitation Spectroscopic System for the Identification and Environmental Monitoring of Algal Cells"; Analytical Chemistry; Aug. 1, 2005; pp. 4955-4961; vol. 77, No. 15; American Chemical Society.

Wood, Bayden R. et al.; "Raman Imaging of Hemozoin Within the Food Vacuole of Plasmodium Falciparum Trophozoites"; FEBS Letters: 27638; 2003; pp. 247-252; vol. 554; Federation of European Biochemical Societies, Elsevier B.V.

Wood, Bayden R. et al.; "Resonance Raman Spectroscopy Provides Evidence of Heme Ordering Within the Functional Erythrocyte"; Vibrational Spectroscopy; 2005; pp. 71-78; vol. 38; Elsevier B.V.

Wood, Bayden R.; McNaughton, Don; "Review: Resonance Raman Spectroscopy in Malaria Research"; Expert Review of Proteomics; Oct. 2006; pp. 525-544; vol. 3, No. 5; Future Drugs Ltd.

Zhang, Yan et al.; "Adaptive Optics Parallel Spectral Domain Optical Coherence Tomography for Imaging the Living Retina"; Optics Express; Jun. 13, 2005; pp. 4792-4811; vol. 13, No. 12; OSA.

PCT International Search Report; International App. No. PCT/US2011/001815; Feb. 14, 2012; pp. 1-2.

Andresen et al.; "Infrared Multiphoton Microscopy: Subcellular-Resolved Deep Tissue Imaging"; Science Direct, Current Opinion in Biotechnology; bearing a date of 2009; pp. 1-9; vol. 20; Elsevier Ltd.; could be located at: www.sciencedirect.com.

Arambage et al.; "Research: Malaria Ookinetes Exhibit Multiple Markers for Apoptosis-Like Programmed Cell Death *in vitro*"; BioMed Central, Parasites & Vectors; bearing a date of 2009; pp. 1-16; vol. 2, No. 32; BioMed Central Ltd.; located at: http://www.parasitesandvectors.com/content/2/1/32.

Bahadur et al.; "Biomaterials and Magnetism"; Sadhana; bearing dates of Jun./Aug. 2003; pp. 639-656; vol. 28, Parts 3 & 4; Printed in India.

Balasubramanian et al.; "Photoacoustic Spectroscopy and its Use in Biology"; Bioscience Reports; bearing a date of 1983; pp. 981-995; vol. 3; The Biochemical Society.

Barcinski et al.; "Apoptosis in Parasites and Parasite-Induced Apoptosis in the Host Immune System: A New Approach to Parasitic Diseases"; Brazilian Journal of Medical and Biological Research; bearing a date of 1999; pp. 395-401; vol. 32, No. 4.

Bélisle et al.; "Sensitive Detection of Malaria Infection by Third Harmonic Generation Imaging"; Biophysical Journal: Biophysical Letters; bearing a date of 2008; pp. L26-L28; The Biophysical Society.

Biagini et al.; "The Digestive Food Vacuole of the Malaria Parasite is a Dynamic Intracellular $Ca^{2+}$ Store"; The Journal of Biological Chemistry; bearing a date of Jul. 25, 2003; pp. 27910-27915; vol. 278, No. 30; The American Society for Biochemistry and Molecular Biology, Inc.; could be located at: www.jbc.org.

Chen et al.; "Epi—Third and Second Harmonic Generation Microscopic Imaging of Abnormal Enamel"; Optics Express; bearing a date of Jul. 21, 2008; pp. 11670-11679; vol. 16, No. 15; OSA.

Chu et al.; "Functional THG Microscopy with Plasmon-Resonance Enhancement in Silver Nanoparticles"; CThPDD7; bearing a date of 2003; pp. 1-2; Optical Society of America.

Clay et al.; "Spectroscopy of Third-Harmonic Generation: Evidence for Resonances in Model Compounds and Ligated Hemoglobin"; J. Opt. Soc. Am. B; bearing a date of May 2006; pp. 932-950; vol. 23, No. 5; Optical Society of America.

Clay et al.; "Ultrafast Third Harmonic Micro-spectroscopy Reveals a Two-Photon Resonance in Human Hemoglobin"; Photonics West; bearing dates of Jan. 22-25, 2006; pp. 1-8; vol. 6108, No. 6108-8.

Cui et al.; "Cytotoxic Effect of Curcumin on Malaria Parasite *Plasmodium falciparum*: Inhibition of Histone Acetylation and Generation of Reactive Oxygen Species"; Antimicrobial Agents and Chemotherapy; bearing a date of Feb. 2007; pp. 488-494; vol. 51, No. 2; American Society for Microbiology.

De Villiers et al.; "Oriented Nucleation of β-Hematin Crystals Induced at Various Interfaces: Relevance to Hemozoin Formation"; Crystal Growth & Design; bearing a date of 2009; pp. 626-632; vol. 9, No. 1; American Chemical Society.

Débarre et al.; "Quantitative Characterization of Biological Liquids for Third-Harmonic Generation Microscopy"; Biophysical Journal; bearing a date of Jan. 2007; pp. 603-612; vol. 92; The Biophysical Society.

Débarre et al.; "Signal Epidetection in Third-Harmonic Generation Microscopy of Turbid Media"; Optics Express; bearing a date of Jul. 9, 2007; pp. 8913-8924; vol. 15, No. 14; OSA.

Ding et al.; "ELF Magnetic Fields Promote $H_2O_2$-Induced Apoptosis and Necrosis and Its Molecular Mechanism"; 3rd International EMF Seminar in China: Electromagnetic Fields and Biological Effects; bearing dates of Oct. 13-17, 2003; pp. 114 (plus cover page), Session 8-7.

Egan, Timothy J.; "Physico-Chemical Aspects of Hemozoin (Malaria Pigment) Structure and Formation"; Journal of Inorganic Biochemistry; bearing a date of 2002; pp. 19-26; vol. 91; Elsevier Science Inc.

Feagin et al.; "Effects of Alternating Magnetic Fields on Malaria Parasites"; 3rd International EMF Seminar in China: Electromagnetic Fields and Biological Effects; bearing dates of Oct. 13-17, 2003; pp. 116 (and cover page), Session 9-1.

Galanzha et al.; "In vivo, Noninvasive, Label-Free Detection and Eradication of Circulating Metastatic Melanoma Cells Using Two-Color Photoacoustic Flow Cytometry with a Diode Laser"; Cancer Res: Cell, Tumor, and Stem Cell Biology; bearing a date of Oct. 15, 2009; pp. 7926-7934; vol. 69, No. 20; American Association for Cancer Research.

Halpern et al.; "Oxymetry Deep in Tissues with Low-Frequency Electron Paramagnetic Resonance"; PNAS, Physiology; bearing a date of Dec. 20, 1994; pp. 13047-13051; vol. 91, No. 26; JSTOR.

Hothi et al.; "Kinetic Isotope Effects and Ligand Binding in PQQ-Dependent Methanol Dehydrogenase"; Biochem. J.; bearing a date of 2005; pp. 123-133; vol. 388; Biochemical Society.

Mao et al.; "Third Harmonic Generation in Self-Focused Filaments in Liquids"; bearing a date of 2007; pp. 1-5; Optical Society of America.

Mungthin et al.; "Central Role of Hemoglobin Degradation in Mechanisms of Action of 4-Aminoquinolines, Quinoline Methanols, and Phenanthrene Methanols"; Antimicrobial Agents and Chemotherapy; bearing a date of Nov. 1998; pp. 2973-2977; vol. 42, No. 11; American Society for Microbiology.

Newman et al.; "A Magneto-Optic Route Toward The In Vivo Diagnosis of Malaria: Preliminary Results and Preclinical Trial Data"; Biophysical Journal; bearing a date of Jul. 2008; pp. 994-1000; vol. 95; Biophysical Society.

Orjih, Augustine U.; "Heine Polymerase Activity and the Stage Specificity of Antimalarial Action of Chloroquine"; The Journal of Pharmacology and Experimental Therapeutics; bearing a date of Mar. 6, 1997; pp. 108-112; vol. 282, No. 1; The American Society for Pharmacology and Experimental Therapeutics.

Orjih, Augustine U.; "On the Mechanism of Hemozoin Production in Malaria Parasites: Activated Erythrocyte Membranes Promote β-Hematin Synthesis"; Exp Bio Med; bearing a date of 2001; pp. 746-752; vol. 226, No. 8; The Society for Experimental Biology and Medicine.

Oron et al.; "Harmonic Generation with Temporally Focused Ultrashort Pulses"; J. Opt. Soc. Am. B; bearing a date of Dec. 2005; pp. 2660-2663; vol. 22, No. 12; Optical Society of America.

Oron et al.; "Third-Harmonic Generation with Cylindrical Gaussian Beams"; J. Opt. Soc. Am. B; bearing a date of Nov. 2004; pp. 1964-1968; vol. 21, No. 11; Optical Society of America.

Pandey et al.; "Mechanism of Malarial Haem Detoxification Inhibition by Chloroquine"; Biochem. J.; bearing a date of 2001; pp. 333-338; vol. 355; Biochemical Society.

Parroche et al.; "Malaria Hemozoin is Immunologically Inert but Radically Enhances Innate Responses by Presenting Malaria DNA to Toll-Like Receptor 9"; PNAS; bearing a date of Feb. 6, 2007; pp. 1919-1924 (plus cover page); vol. 104, No. 6; The National Academy of Sciences of the USA; located at: www.pnas.org/cgi/doi/10.1073/pnas.0608745104.

Ribaut et al.; "Methodology: Concentration and Purification by Magnetic Separation of the Erythrocytic Stages of all Human *Plasmodium* Species"; BioMed Central, Malaria Journal; bearing a date of Mar. 5, 2008; 5 pages; vol. 7, No. 45; BioMed Central Ltd.

Sheetz et al.; "Ultrafast Optics: Imaging and Manipulating Biological Systems"; Journal of Applied Physics, Applied Physics Reviews—Focused Review; bearing a date of 2009; pp. 051101-1 through 051101-17; vol. 105, No. 051101; American Institute of Physics.

Sienkiewicz et al.; "Multi-Frequency High-Field EPR Study of Iron Centers in Malarial Pigments"; JACS Communications; bearing a date of 2006; pp. 4534-4535; vol. 128; American Chemical Society.

Squier et al.; "Third Harmonic Generation Microscopy"; Optics Express; bearing a date of Oct. 26, 1998; pp. 315-324; vol. 3, No. 9; Optical Society of America.

Tai et al.; "*In vivo* Optical Biopsy of Hamster Oral Cavity with Epi-Third-Harmonic-Generation Microscopy"; Optics Express; bearing a date of Jun. 26, 2006; pp. 6178-6187; vol. 14, No. 13; Optical Society of America.

Tai et al.; "*In vivo* Molecular-Resonant Third Harmonic Generation Microscopy of Hemoglobin"; CTuF4.pdf; bearing a date of 2007; pp. 1-2; Optical Society of America.

"Third Harmonic Generator"; Del Mar Photonics, Instruction Manual; pp. 1-17; Model ATsG800-7.

Wang et al.; "Evaluation of a Multi-Wavelength Reflectance System for Determination of Tissue Optical Properties in the UVA-VIS"; CFC5.pdf; bearing a date of 2007; pp. 1-2; Optical Society of America.

Yelin et al.; "Third-Harmonic Microscopy with a Titanium-Sapphire Laser"; Applied Physics B, Lasers and Optics; bearing a date of 2002; pp. S97-S101; vol. 74; Springer-Verlag.

Yelin et al.; "Laser Scanning Third-Harmonic-Generation Microscopy in Biology"; Optics Express; bearing a date of Oct. 11, 1999; pp. 169-175; vol. 5, No. 8; Optical Society of America.

Zheng et al.; "Multichannel Multiphoton Imaging of Metal Oxides Particles in Biological System"; Proceeding of SPIE; bearing a date of 2004; 9 pages; Paper 5323-55.

Zimmerman et al.; "Diagnosis of Malaria by Magnetic Deposition Microscopy"; Am. J. Trop. Med. Hyg.; bearing a date of 2006; pp. 568-572; vol. 74, No. 4; The American Society of Tropical Medicine and Hygiene.

Zoueu et al.; "Optical Microscope Based on Multispectral Imaging Applied to Plasmodium Diagnosis"; Journal of Applied Sciences; bearing a date of 2008; pp. 2711-2717; vol. 8, No. 15; Asian Network for Scientific Information.

PCT International Search Report; International App. No. PCT/US 11/00259; bearing a date of Jun. 20, 2011; pp. 1-4.

PCT International Search Report; International App. No. PCT/US 2011/000260; bearing a date of Jun. 20, 2011; pp. 1-4.

Jamjoom, G.A.; "Dark-field microscopy for detection of malaria in unstained blood films"; Journal of Clinical Microbiology; bearing a date of May 1983; pp. 717-721 and cover page; vol. 17, No. 5; American Society for Microbiology.

"Magnetic fields may hold key to malaria treatment, UW researchers find"; UW Today; bearing a date of Mar. 30, 2000; pp. 1-2; University of Washington News Archives.

* cited by examiner

SPECTROSCOPIC DETECTION OF MALARIA VIA THE EYE

SUMMARY

The present application relates, in general, to systems, methods, and apparatus for identifying hemozoin in ocular blood vessels, as well as systems, apparatus, and methods for diagnosing malarial infections at least partially based on detection of hemozoin in ocular blood vessels. Such systems and methods may be performed using one or more ophthalmic apparatus and/or devices configured to detect Raman scatter and electromagnetic energy emitted from the ocular blood vessels. Such systems, apparatus, and methods may include programming implementations for hemozoin identification and/or malaria diagnosis.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
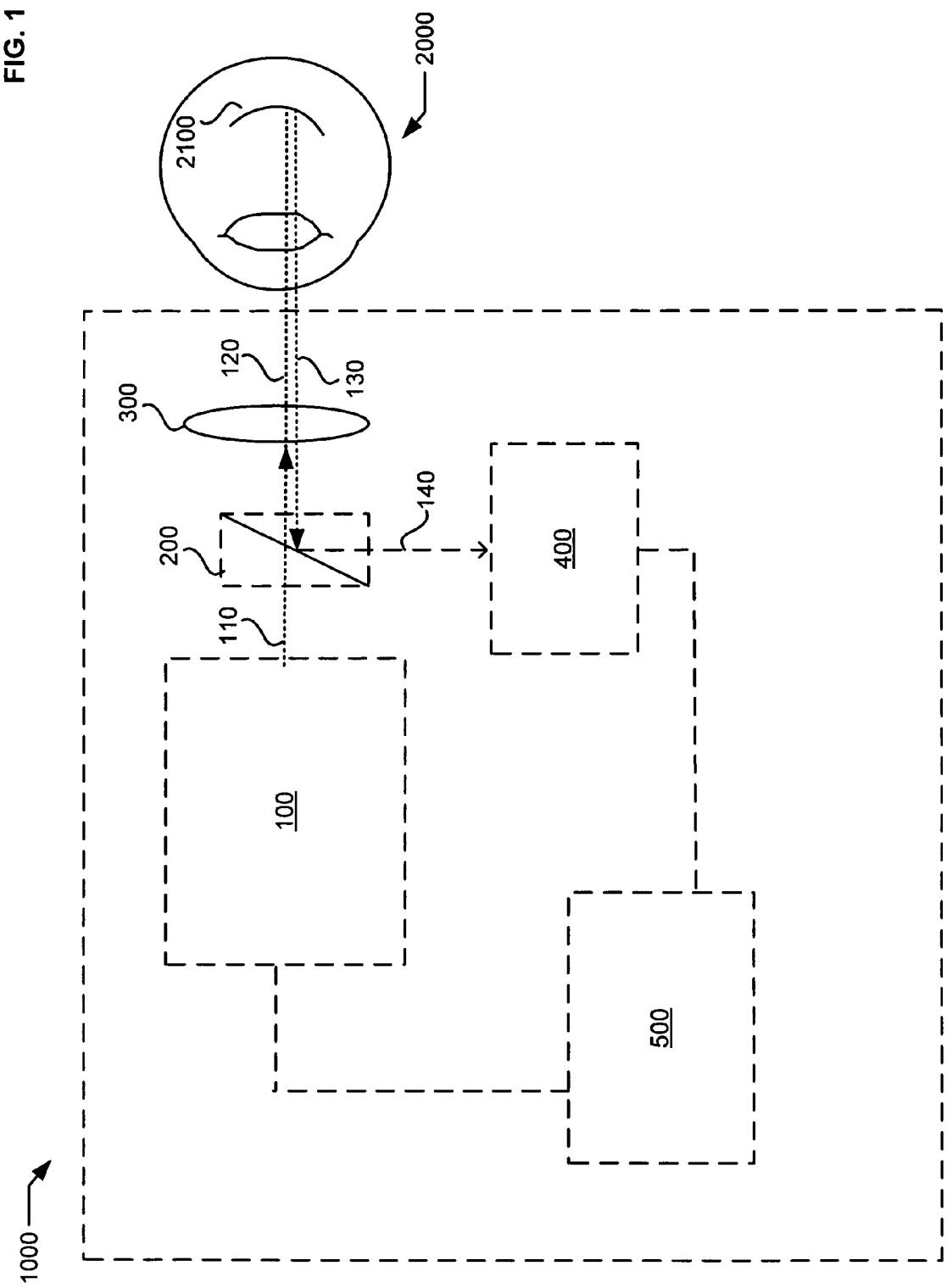
FIG. 1 is a schematic of an optional embodiment of a spectral imaging and/or optical system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application relates, in general, to systems, apparatus, and methods for identifying hemozoin in ocular blood vessels, as well as systems, apparatus, and methods for diagnosing malarial infections at least partially based on detection of hemozoin in ocular blood vessels. Those having skill in the art will appreciate that the specific systems, apparatus, devices, and methods described herein are intended as merely illustrative of their more general counterparts.

Malaria is still one of the most important infectious diseases in terms of human impact, including morbidity and mortality. About 40% of the world's population is at risk for disease, and up to 3 million people die yearly from malaria. Malaria in humans is caused by one or more *Plasmodium* spp., including but not limited to, *P. vivax, P. falciparum, P. malariae*, and *P. ovale*. Other *Plasmodium* spp. infect a variety of other animals, any of which species may be detected using one or methods described herein.

Malaria infection in humans is traditionally detected by microscopic examination of blood films (thick and/or thin) by trained professionals (e.g. technicians, physicians, nurses, or other health-care workers as appropriate). *Plasmodium* infect erythrocytes in the human host, although they can be found in other cells, including but not limited to, white blood cells. In the red blood cells, free toxic heme is generated during degradation of host hemoglobin by the parasite, and is detoxified by sequestration as hemozoin, an inert, crystalline substance concentrated in the parasite food vacuole.

As used herein, the term "parasitemia" refers to the percentage of malaria-infected red blood cells. Parasitemias may range from 0.0001-0.0004% (5-20 parasites/µl of blood—limit of detection using standard techniques), 0.002% (100 parasites/µl of blood—may be symptomatic below this level), 0.2% (10,000 parasites/µl of blood—immune patients will exhibit symptoms), 2% (100,000 parasites/µl of blood—max. parasitemia of *P. vivax* & *P. ovale*), 2-5% (100,000 to 250,000 parasites/µl of blood—hyperparasitemia, increased mortality), and 10% (500,000 parasites/µl of blood—high mortality). In general, the greater the parasite density in the peripheral blood, the greater the likelihood that severe disease is present or will develop.

In one aspect, the disclosure is drawn to one or more methods for identifying hemozoin optionally using one or more optical device or apparatus. Although one or more methods may be presented separately herein, it is intended and envisioned that one or more methods and/or embodiments of one or more methods may be combined and/or substituted to encompass the full disclosure. In some embodiments, one or more methods may include one or more operations, and be implemented using one or more computing devices and/or systems.

Embodiments include one or more methods including: providing electromagnetic energy to one or more ocular blood vessels, the electromagnetic energy configured to induce Raman scattering; optionally selectively detecting one or more characteristics of an electromagnetic response associated with provided electromagnetic energy and substantially localized to the one or more ocular blood vessels; optionally tracking one or more indicators of blood flow in the one or more ocular blood vessels at least partially based on detecting one or more characteristics of an electromagnetic response associated with provided electromagnetic energy; and detecting a Raman spectral response for hemozoin associated with the one or more ocular blood vessels.

In some embodiments, one or more methods include providing one or more of electromagnetic energy configured to induce Raman scattering in ocular blood vessels, electromagnetic energy configured for localization of ocular blood vessels, and/or electromagnetic energy configured for tracking one or more indicators of blood flow. In some embodiments, the electromagnetic energy provided for localization and/or tracking and the electromagnetic energy provided for Raman scattering are the same. In some embodiments, the electromagnetic energy provided for localization and/or tracking and the electromagnetic energy provided for Raman scattering are different. In some embodiments, the electromagnetic energy provided for localization and the electromagnetic energy provided for tracking are the same. In some embodiments, the electromagnetic energy provided for localization and the electromagnetic energy provided for tracking are different.

Electromagnetic energy may be provided from one source, from two sources, from three sources, from more than one source, from two or more sources, or from three or more sources. Sources for providing electromagnetic energy may include, but are not limited to, lasers, LEDs, fluorescent lamps, and incandescent lamps, among others. Additional sources for providing electromagnetic energy are known in the art and/or described herein.

As used herein, the term "identifying hemozoin" includes, but is not limited to, detecting a spectral signature characteristic for hemozoin optionally using Raman scattering. As used herein, "Raman scattering" includes, but is not limited to, inelastic scattering of light (optionally monochromatic), optionally generated by electromagnetic energy provided by a laser in one or more wavelengths of the visible, infrared, or ultraviolet ranges (optionally near infrared and/or near ultraviolet). The provided electromagnetic energy interacts with elements and/or modes in the system, resulting in the provided energy being shifted up and/or down. The shift in energy provides information about the elements and/or modes of the system.

For the spontaneous Raman effect, a molecule may be excited from the ground state to a virtual energy state, then relax into a vibrational excited state, which generates Stokes-Raman scattering. If the molecule is already in an elevated vibrational energy state, Raman scattering is anti-Stokes Raman scattering. A molecular polarizability change, or amount of deformation of the electron cloud, with respect to the vibrational coordinate is associated with the Raman effect. The amount of the polarizability change will determine intensity, whereas the Raman shift is associated with the vibrational level.

In illustrative embodiments, the back of the eye, optionally the retina, including the ocular blood vessels, is illuminated using a laser beam. Returning light passes through a lens, and wavelengths close to the provided light (associated with elastic Rayleigh Scattering) are filtered out and/or passed to a non-Raman detector. The rest of the collected light is passed to a detector, optionally a photomultiplier tube (PMT) and/or a charge-coupled device (CCD) detector to determine the Raman shift.

In some embodiments, the electromagnetic energy configured to induce Raman scattering is provided at wavelengths of less than approximately 5 µm, less than approximately 4.5 µm, less than approximately 4 µm, less than approximately 3.5 µm, less than approximately 3 µm, less than approximately 2.5 µm, less than approximately 2 µm, less than approximately 1.5 µm, than approximately 1.0 µm, less than approximately 0.5 µm, and/or less than approximately 0.25 µm. In some embodiments, the electromagnetic energy is provided at wavelengths of approximately 0.25 µm to 5.0 µm, 0.25 µm to 4.0 µm, 0.25 µm to 3.0 µm, 0.25 µm to 2.0 µm, 0.25 µm to 1.0 µm, 0.25 µm to 0.5 µm, approximately 0.4 µm to 5 µm, approximately 0.4 µm to 4 µm, approximately 0.4 µm to 3 µm, approximately 0.4 µm to 1.5 µm, approximately 0.4 µm to 1.0 µm, approximately 1 µm to 5 µm, approximately 1 µm to 4 µm, approximately 1 µm to 3 µm, approximately 1 µm to 2 µms, approximately 2 µm to 5 µm, approximately 2 µm to 4 µms, approximately 2 µms to 3 µm, approximately 3 µm to 5 µm, approximately 3 µm to 4 µm, and/or approximately 4 µm to 5 µm.

In some embodiments, the electromagnetic energy configured to induce Raman scattering is provided in short pulses. In illustrative embodiments, a short pulse having approximately the energy of a longer pulse provides an enhanced Raman scatter as compared with the longer pulse. In some embodiments, the short pulses are sub microsecond pulses, sub nanosecond pulses, sub picosecond pulses, and/or sub femtosecond pulses. In some embodiments, the short pulses are approximately microsecond pulses, approximately nanosecond pulses, approximately picosecond pulses, and/or approximately femtosecond pulses. Sources of electromagnetic energy capable of providing short pulses of energy are known in the art and/or described herein and include, but are not limited to lasers and LEDs.

In some embodiments, the electromagnetic energy configured to induce Raman scattering is provided at an energy approximately equal to an electronic energy transition in hemozoin. In resonance Raman spectroscopy, the excitation wavelength is approximately matched to an electronic transition of a molecule (e.g. hemozoin), to enhance vibrational modes associated with the excited electronic state. The Raman shift of hemozoin associated with a variety of wavelengths has been recorded (see, e.g., Wood & McNaughton. (2006) Expert Rev. Proteomics 3:525-544).

In some embodiments, the electromagnetic energy configured to induce Raman scattering is provided in one or more ranges of approximately 530 nm through approximately 580 nm, approximately 400 nm through approximately 450 nm, or approximately 800 nm through approximately 860 nm. In some embodiments, the electromagnetic energy configured to induce Raman scattering is provided at approximately 400 nm, 410 nm, 420 nm, 430 nm, 440 nm, 450 nm, 460 nm, 480 nm, 510 nm, 530 nm, 540 nm, 550 nm, 560 nm, 570 nm, 580 nm, 630 nm, 780 nm, 800 nm, 810 nm, 820 nm, 830 nm, 840 nm, and/or 850 nm.

Embodiments of one or more methods include detecting a Raman spectral response for hemozoin. Raman spectral responses may be detected using direct imaging, where a field is examined for scattering over a (optionally small) range of wavenumbers (Raman shifts), or using hyperspectral (or chemical) imaging in which (optionally hundreds, thousands, etc.) spectra are acquired from a field. Chemical imaging includes the approximately simultaneous acquisition of spectra and spatial information. Instrumentation may include, but is not limited to, an electromagnetic source to illuminate the sample (e.g. ocular blood vessels), a spectrally selective element, and a detector (e.g. CCD and/or PMT). Signal and/or image processing techniques may be used to discriminate spectra of interest (e.g. hemozoin-related) from spectra from other constituents in the field, including for example, but not limited to, fluids, cells, hemoglobin, and other proteins, lipids, and nucleic acids.

Raman spectral responses for hemozoin are known in the art and are detectable from malaria-infected red blood cells (see, e.g., Wood & McNaughton. (2006) Expert Rev. Proteomics 3:525-544; Tripathi et al. (2004) Anal. Biochem. 325:85-91; Egan et al. (2006) FEBS Letters 580:5105-5110; Tekwani & Walker. (2005) Combinatorial Chem. & High Throughput Screening 8:63-79; Slater et al. (1991) Proc. Natl. Acad. Sci. USA 88:325-329; Frosch et al. (2007) J. Phys. Chem. B 111:11047-11056; Wood et al. (2005) Vibrational Spectroscopy 38:71-78; and Wood et al. (2003) FEBS Letters 554:247-252).

In some embodiments, a Raman spectral response for hemozoin is optionally detected from approximately 1700 $cm^{-1}$ through approximately 1000 $cm^{-1}$. In some embodiments, Raman spectral response for hemozoin is optionally detected at one or more ranges including approximately 1620 $cm^{-1}$ through approximately 1680 $cm^{-1}$, approximately 1200 $cm^{-1}$ through approximately 1250 $cm^{-1}$, approximately 1350 $cm^{-1}$ through approximately 1400 $cm^{-1}$, approximately 1620 $cm^{-1}$ through approximately 1630 $cm^{-1}$, approximately 1565 $cm^{-1}$ through approximately 1575 $cm^{-1}$, approximately 1545 $cm^{-1}$ though approximately 1555 $cm^{-1}$, approximately 1540 $cm^{-1}$ through approximately 1550 $cm^{-1}$, approximately 1540 $cm^{-1}$ through approximately 1630 $cm^{-1}$, and/or approximately 1370 $cm^{-1}$ through approximately 1380 $cm^{-1}$. In some embodiments, Raman spectral response for hemozoin is optionally detected at approximately 1375 $cm^{-1}$, at approximately 1492 $cm^{-1}$, at approximately 1550 $cm^{-1}$, at approximately 1571 $cm^{-1}$, and/or approximately 1628 $cm^{-1}$.

As used herein, the Raman energy shift is provided as a wavenumber in units of $cm^{-1}$ (e.g., 1374 $cm^{-1}$ for one of the strong hemozoin lines). This information may also be provided as a photon frequency shift by multiplying the wavenumber by c, the speed of light (e.g., 1374 cm$^{-1}$ becomes 41.2 THz). An equivalent way to express this is in energy terms; the photon energy shift in electron-volts is the wavenumber shift multiplied by 0.000124 (e.g., 1374 cm$^{-1}$ correlates to 0.17 eV).

In some embodiments, one or more methods include detecting a Raman spectral response for hemozoin optionally associated with the one or more ocular blood vessels. In illustrative embodiments, electromagnetic energy configured to induce a Raman spectral response from hemozoin is provided to the back of the eye, the resulting back scatter is acquired, and is filtered and/or analyzed such that additional processing related to detection of hemozoin-specific spectra is performed on spectra approximately associated with the one or more ocular blood vessels. In illustrative embodiments, electromagnetic energy configured to induce a Raman spectral response from hemozoin is provided specifically to areas approximating the location of one or more ocular blood vessels, the resulting back scatter is acquired, and analyzed and/or processed to detect the presence and/or absence of hemozoin-specific spectra. In some embodiments, locations of the one or more ocular blood vessels are predicted based, for example, on known vascularization of the eye. In some embodiments, locations of the one or more ocular blood vessels are determined either concurrently or in advance, based, for example, on non-Raman spectra acquired from the eye and processing to detect one or more characteristics of ocular blood vessels, including but not limited to, structure, size, depth, branching, and location.

As used herein, the term "hemozoin-specific and/or hemozoin-indicative signature" includes, but is not limited to a Raman spectra that may be used to indicate and/or detect the presence of hemozoin in situ, despite the presence of backscatter from other molecules, such as but not limited to those in one or more ocular blood vessels, optionally in one or more blood cells, optionally in one or more red blood cells and/or one or more white blood cells. In illustrative embodiments, illumination provided at 780 nm to a malaria-infected red blood cell enables detection of hemozoin over hemoglobin by enhanced Raman using the distinctive peak at 1374 cm$^{-1}$ (see, e.g., Wood et al. (2003) FEBS Letters 554:247-252).

In some embodiments, a Raman spectral response for hemozoin is optionally detected by capturing selected spectra from the Raman spectral response, wherein the selected spectra includes a hemozoin-specific signature. In illustrative embodiments, one or more Raman detectors are calibrated and/or programmed to capture spectra associated with hemozoin, and not other spectra, and optionally only specific spectra or spectral ranges associated with hemozoin. In some embodiments, a Raman spectral response for hemozoin is optionally detected by analyzing the Raman spectral response for selected spectra, wherein the selected spectra include a hemozoin-specific signature. In illustrative embodiments, one or more Raman detectors are calibrated and/or programmed to capture Raman spectra, but not necessarily limited to acquiring Raman spectra associated with hemozoin; the acquired spectra is analyzed to determine the presence or absence of spectra associated with hemozoin.

In some embodiments, the one or more methods optionally include automatically processing the detected Raman spectral response. In illustrative embodiments, one or more methods include the operation processes, computer programs and/or computer systems hardware for performing analyses of spectral data, optionally automatically, optionally programmably, and/or optionally remotely. These operations may be performed by circuitry integral to the device for detecting Raman spectra, or by circuitry not integral to such device. Such circuitry may be remotely located, or in computing systems hard wired to and/or wirelessly associated with such device. Circuitry that can process signals and/or data may be implemented in hardware and/or software known in the art and/or described herein. Additionally, such processing may also include or be supplemented by optical components, elements, or subsystems, such as filters, spectrally responsive elements (e.g., wavelength division demultiplexers), or other optically responsive structures.

In some embodiments, the one or more methods optionally include optionally correlating and/or associating the detected Raman spectral response with malaria infection. Hemozoin is the "malaria pigment" characteristic of malaria infections. Identification of hemozoin-specific spectra will be associated with malaria infection. Processing of the spectra to determine the approximate locations of the hemozoin-specific responses provides an estimate of the number of malaria-infected red blood cells in a scan or field (e.g. in the ocular blood vessels in the back of the eye). The approximate parasitemia can be calculated, for example, based on the estimated, predicted, or determined numbers of red blood cells in the same field and/or scan.

In some embodiments, one or more methods optionally include providing electromagnetic for localization of one or more ocular blood vessels, and/or optionally providing electromagnetic energy for tracking blood flow in one or more blood vessels.

As used herein, the term "electromagnetic energy" may include one or more frequencies having one or more characteristics that taken as a whole are not considered unduly harmful to the eye by physicians with skill in the art (e.g. ophthalmologists). In illustrative examples, such electromagnetic energy may include frequencies of optical light, optionally including visible light (detected by the human eye between approximately 400 nm and 700 nm) as well as infrared (longer than 700 nm) and limited spectral regions of ultraviolet light, such as UVA light (between approximately 320 nm and 400 nm). Electromagnetic or optical energy is made up of photons. Electromagnetic energy includes, but is not limited to, single photon electromagnetic energy, two photon electromagnetic energy, multiple wavelength electromagnetic energy, and extended-spectrum electromagnetic energy.

Electromagnetic energy may be configured as a continuous beam or as a train of short pulses. In the continuous wave mode of operation, the output is relatively consistent with respect to time. In the pulsed mode of operation, the output varies with respect to time, optionally having alternating 'on' and 'off' periods. Electromagnetic energy may be provided by one or more lasers, for example, having one or more of a continuous or pulsed mode of action. One or more pulsed lasers may include, but are not limited to, Q-switched lasers, mode locking lasers, and pulsed-pumping lasers. Mode locked lasers emit extremely short pulses on the order of tens of picoseconds down to less than 10 femtoseconds, the pulses optionally separated by the time that a pulse takes to complete one round trip in the resonator cavity. Due to the Fourier limit, a pulse of such short temporal length may have a spectrum which contains a wide range of wavelengths.

In some embodiments, the electromagnetic energy is focused at a depth of approximately 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, or 3.0 mm below the surface of the back of the eye, beyond the surface of a wall of a blood vessel wall, and/or beyond a surface of an internal location. In some embodiments, the electromagnetic energy is focused at a depth of approximately 0.1 to 3 mm, 0.1 to 2.5 mm, 0.1 to 2.0 mm, 0.1 to 1.5 mm, 0.1 to 1.0 mm, 0.1 to 0.5 mm, 0.5 to 3.0 mm, 0.5 to 2.5 mm, 0.5 to 2.0 mm, 0.5 to 1.5 mm, 0.5 to 1.0 mm, 1.0 to 3.0 mm, 1.0 to 2.5 mm, 1.0 to 2.0 mm, 1.0 to 1.5 mm, 1.5 to 3.0 mm, 1.5 to 2.5 mm, 1.5 to 2.0 mm, 2.0 to 3.0 mm, 2.0 to 2.5 mm, or 2.5 to 3.0 mm below the surface of the back of the eye, beyond the surface of a wall of a blood vessel wall, and/or beyond a surface of an internal location.

In some embodiments, the electromagnetic energy is generated by two photons having the same wavelength or substantially the same wavelength. In some embodiments, the electromagnetic energy is generated by sets of two photons having different wavelengths. Electromagnetic energy at the energy levels of the two photons is optionally focused at a depth below the surface of the back of the eye, beyond the surface of a wall of a blood vessel wall, and/or beyond a surface of an internal location, and/or optionally at one or more depths. As used herein, the term "two-photon" may include excitation optionally using one or more femtosecond lasers. In some embodiments, two photon electromagnetic energy is coupled through a virtual energy level and/or coupled through an intermediate energy level.

As used herein, the term "extended-spectrum" may include a range of possible electromagnetic radiation wavelengths within the full spectrum of possible wavelengths, optionally from extremely long to extremely short and optionally including wide spectrum and narrow spectrum wavelengths. One of skill in the art is able to select appropriate ranges for the methods disclosed herein based on information publicly available and/or disclosed herein.

In some embodiments, the electromagnetic energy may be defined spatially and/or directionally. In some embodiments, the electromagnetic energy may be spatially limited, optionally spatially focused and/or spatially collimated. In some embodiments, the electromagnetic energy may be directionally limited, directionally varied, and/or directionally variable. In illustrative embodiments, the electromagnetic energy optionally contacts less than less than an entire possible area, or an entire possible target, and/or is limited to a certain depth within a tissue. In illustrative embodiments, the electromagnetic energy is spatially and/or directionally limited so that only areas approximately bounding the walls of the one or more ocular blood vessels are provided with electromagnetic energy. In illustrative embodiments, the electromagnetic energy may be provided over an entire field (e.g. scanning across the back of the eye, e.g. retina), through movement of the electromagnetic source, and/or through illumination from more than one, two, three, four, and/or multiple sources in the device. Alternatively, in some approaches illumination may be provided over less than an entire field, for example, by illuminating according to a vector scanning approach. In such approaches, illumination energy may be directed to less than all of the area, e.g. primarily in and/or around vascular regions or in areas of interest, such as areas where blood components of interest may be suspected to be or predicted to be. Alternatively, such illumination of less than the entire region may be implemented by a scanning pattern encompassing the entire region combined with activating the source of electromagnetic energy only in selected locations.

In illustrative embodiments, the electromagnetic energy may be provided using one or more scanning beam systems positioned for viewing by a viewer's eye (see, e.g. U.S. 2006/0284790 A1 and/or U.S. 2005/0020926 A1). The scanning system device may include control electronics to control the operation of the light source that outputs modulated light beams, as well as to control the detection of the light reflected from the target. The light source may utilize coherent light emitters, such as laser diodes or microlasers, or may use non-coherent sources such as light emitting diodes. The light source may include directly modulated light emitters, such as light emitting diodes (LEDs, optionally red, green and/or blue) or may include continuous light emitters indirectly modulated by external modulators, such as acousto-optic modulators.

As part of the optical/spectral system, the scanning system device may include a scanning assembly that scans the modulated beams though two-dimensional scanning patterns, such as raster patterns. In illustrative embodiments, the scanning system device simultaneously scans beams of light along substantially continuous scan paths. The scanning assembly optionally includes one or more periodically scanning mirrors that optionally pivot to sweep the beams horizontally and/or vertically. A mechanically resonant scanner produces the horizontal component by scanning the beam sinusoidally. A non-resonant or semi-resonant scanner typically scans the beam vertically with a substantially constant angular speed. In illustrative embodiments, the scanning mechanism optionally includes a biaxial microelectromechanical (MEMs) scanner which is optionally also a resonant scanner that optionally has a characteristic resonant frequency, or optionally a tunable resonant frequency. In some approaches, the scanner may be resonant about two or more axes. In other approaches, the scanner may be resonant about one or more axes and nonresonant about one or more other axes. In still another approach, more than one scanner may be cooperatively provide scanning for the scanning system device. A variety of approaches may be used for tuning including, but not limited to, fabrication with integral tuning tabs, where the resonant frequency is below the desired resonant frequency, followed by laser trimming, laser ablation, or mechanical force to reduce the mass. MEMs scanners may, for example, be tuned using laser ablation.

The system may include lenses optionally positioned on opposite sides of the scanning assembly or other optical elements (e.g. a beamsplitter and lens) and including diffractive elements (e.g. Fresnel lenses) to guide and shape the light. The lenses are optionally cylindrical graded index (GRIN) lenses, or doublet or triplet lenses, that gather and shape light from the light source. Where the light source includes optical fibers that feed the lenses, the lenses are optionally bonded to or integral with the fibers. After leaving the lens, or equivalent optical element, the scanning beams enter the eye through a pupil and strike the retina or back of the eye, including one or more ocular blood vessels.

The system optionally includes one or more of polarization sensitive materials, chromatic correction, or other optical techniques for controlling the shape, phase or other characteristics of the light in the overall optical train. Other optical elements such as, but not limited to, polarizers, color filters, exit pupil expanders, chromatic correction elements, eye-tracking elements, and background masks may be incorporated for certain application as appropriate.

The system optionally includes one or more detectors and/or imagers, such as, but not limited to, PMTs and/or CCDs for capturing reflected light and/or for capturing Raman back scatter as discussed herein. In illustrative embodiments, for each location in the field, one or more detectors optionally selectively detects light at the wavelength, polarization, or other characteristic of its corresponding source, according to the reflectivity of the respective location. The detectors output electrical signals to decoding electronics that store data representative of the reflected light.

The system is optionally configured for table top use (e.g. scanning laser ophthalmoscope), wall-mounted, as a handheld device, as a portable device, or for mobile personnel use such as, but not limited to, mounted on a helmet, a hat, and/or glasses. In some embodiments, select portions of the device are handheld or designed for mobile use, such as, for example, the light source and detector, and other portions are optionally linked by fiber optic and electronic tether (optionally carried separately, such as attached to a hip belt, or in a pocket), and/or optionally linked through wireless communication.

As described for providing electromagnetic energy configured to induce Raman scattering, above, in some embodiments, one or more of the electromagnetic energy provided for localization and/or the electromagnetic energy provided for tracking, are provided to one or more ocular blood vessels at least partially based on one or more of a predicted location or a detected location of the one or more ocular blood vessels. Embodiments of one or more methods optionally include analyzing the one or more characteristics of the electromagnetic response to determine locations of the one or more ocular blood vessels. In some embodiments, the electromagnetic response is analyzed to determine locations of the one or more ocular blood vessels in advance, concurrently with, and/or after the other measurements (e.g. Raman scatter and/or tracking).

In some embodiments, one or more methods include selectively detecting one or more characteristics of an electromagnetic response associated with provided electromagnetic energy and optionally substantially localized to the one or more ocular blood vessels, optionally at least partially based on one or more of a predicted or a detected location of the one or more ocular blood vessels. In illustrative embodiments, the electromagnetic energy is selectively detected from areas associated with the one or more ocular blood vessels, rather than from areas throughout the back of the eye (e.g. retina). The programming of the circuitry to capture this information may be based on predicted locations (approximate) of vasculature in the eye, and/or detected locations of vasculature in the eye. Locations optionally include spatial extent, e.g. 3-dimensional including depth of tissue.

As used herein, the term "substantially localized to the one or more ocular blood vessels" may include areas extending beyond the exact spatial extent of the one or more ocular blood vessels. Such additional spatial extent may be determined in a variety of ways and include a variety of distances. In illustrative embodiments, the electromagnetic response is selectively detected within one or more of an expected electromagnetic energy scattering distance from the one or more ocular blood vessels, an expected electromagnetic energy absorption distance from the one or more ocular blood vessels, and/or an area of relative local intensity of the electromagnetic energy associated with the one or more ocular blood vessels. Methods for determining each of these areas are known in the art and/or described herein.

In some embodiments, the electromagnetic response is selectively detected within an area encompassing the one or more ocular blood vessels and radially extending 0.001 to 1.0 mm from the walls of the one or more ocular blood vessels. In some embodiments, the area extends approximately 0 to 1.0 mm, 0 to 0.5 mm, 0 to 0.1 mm, 0 to 0.05 mm, 0 to 0.01 mm, 0 to 0.005 mm, 0 to 0.001 mm, 0.001 to 0.5, 0.001 to 0.1 mm, 0.001 to 0.05 mm, 0.001 to 0.01 mm, 0.001 to 0.005 mm, 0.005 to 0.5, 0.005 to 0.1 mm, 0.005 to 0.05 mm, 0.005 to 0.01 mm, 0.01 to 0.5 mm, 0.01 to 0.1 mm, 0.01 to 0.05 mm, 0.05 to 0.5 mm, 0.05 to 0.1 mm, and/or 0.1 to 0.5 mm from the walls of the one or more ocular blood vessels.

In some embodiments, the electromagnetic response is selectively detected within an area encompassing the one or more ocular blood vessels and radially extending from the walls of the one or more ocular blood vessels an additional approximately 1 to 100%, 1 to 75%, 1 to 60%, 1 to 50%, 1 to 40%, 1 to 30%, 1 to 20%, 1 to 10%, 1 to 5%, 5 to 100%, 5 to 75%, 5 to 60%, 5 to 50%, 5 to 40%, 5 to 30%, 5 to 20%, 5 to 10%, 10 to 100%, 10 to 75%, 10 to 60%, 10 to 50%, 10 to 40%, 10 to 30%, 10 to 20%, 20 to 100%, 20 to 75%, 20 to 60%, 20 to 50%, 20 to 40%, 20 to 30%, 30 to 100%, 30 to 75%, 30 to 60%, 30 to 50%, 30 to 40%, 40 to 100%, 40 to 75%, 40 to 60%, 40 to 50%, 50 to 100%, 50 to 75%, 50 to 60%, 60 to 100%, and/or 60 to 75% of the radius of the lumens of the one or more ocular blood vessels.

Embodiments of one or more methods optionally include tracking one or more indicators of blood flow (optionally blood cells) in the one or more ocular blood vessels. Such tracking may be useful in a variety of approaches. For example, information relating to location of an item of interest (e.g., an individual blood cell, group of blood cells, or other tight or loose grouping of biomaterial within vasculature) can be used to increase an effective duration of imaging of the item of interest. This in turn may be used to increase signal to noise ratio, to increase localization of illumination to the item of interest, or to correlate image data to the items of interest.

In some embodiments, one or more blood cells are tracked at least partially based on one or more of a predicted and/or a detected flow of the one or more blood cells in the one or more ocular blood vessels. In some embodiments, one or more indicators of blood flow velocity in the one or more ocular blood vessels are tracked optionally using Doppler effect optionally generated or induced by one or more of ultrasound, electromagnetic energy, and/or acoustic energy. Color Doppler imaging can be used to provide an ultrasonic measurement of flow velocity within blood vessels of the eye (see, e.g., Williamson et al. (1996) Surv. Ophthalmol. 40:255-67).

While the description of the illustrative embodiment above includes "tracking" of one or more indicators of blood flow, a variety of approaches may provide information useful in processing. For example, such tracking may include predicting flows through vasculature based upon the vascular structure and approximate velocity of blood flow. Such systems may utilize computer modeling of fluid flows or similar techniques for tracking and/or predicting movement in fluid systems.

Responsive to such predicting, the imaging/optical system and/or detection subsystem may concentrate upon items of interest according to the tracking. In one approach, the scanning/projection system and/or imaging/optical system may selectively or locally illuminate the one or more indicators of blood flow, or other items of interest, according to the tracking. Such an approach may increase the effective illumination of the one or more indicators of blood flow or other items of interest without significantly increasing the overall amount of optical energy striking the retina, or other areas. Such tracking may provide freedom in system design by allowing the system to concentrate illumination, processing power, and/or other aspects. Moreover, in some cases, localization of the system concentration may provide additional flexibility in optical system designed for illumination and/or imaging.

Additionally, although tracking and the illustrative example above utilizes response of the imaging/optical system and/or scanning/projection system, such tracking may be implemented substantially within the control system (e.g. control electronics) and/or detection subsystem. For example, tracking may be implemented by identifying patterns of information within acquired image data according to known approaches of tracking and/or identifying objects moving within an image field of an imaging system or in a computer-generated image field. Such approaches have been implemented for example in systems used for target acquisition.

In illustrative embodiments, laser Doppler flowmetry (LDF) is used to measure blood flow in ocular blood vessels using the Doppler shift in laser light scattered by moving erythrocytes (see, e.g., Beare et al. (2006) J. Neurol. Neurosurg. Psych. 77:1288-1290). The microcirculation can also be measured by directing the laser light away from visible blood vessels. The mean relative blood velocity and volume are computed from the spectrum of Doppler frequency shifts. The volume is derived from the width of the Doppler shift spectrum, and the velocity from the magnitude of Doppler shifts.

Embodiments of one or more methods include analyzing the one or more characteristics of the electromagnetic response associated with the provided electromagnetic energy to determine one or more blood flow characteristics of the one or more ocular blood vessels. In some embodiments, analyzing includes comparing the determined one or more blood flow characteristics with one or more expected and/or predicted blood flow characteristics. In some embodiments, the expected characteristics include the expected characteristics for one or more of a non-infected (or control) subject and/or a malaria-infected subject. Expected characteristics for an infected subject, would include one or more of locally and/or regionally altered blood flow (e.g., velocity and/or path). In some instances fluid flow may increase in some areas, and decrease in other areas, optionally depending on the initial width of the vascular and the resultant narrowing. In some instances, cell flow rates may vary, with some cells decreasing in flow rate (those with adhesion molecules, and/or forming rosettes, for example), while others are unaffected.

As used herein, the terms "increase" and "decrease" as related to fluid flow and/or blood flow in ocular blood vessels refer to changes in the speed and/or velocity of the flow (e.g. the fluid or the constituents in the fluid, e.g. cells and macromolecules). Such changes can be up or down, and can be measured using methods known to those of skill in the art and/or described herein. In illustrative embodiments, such changes are detected as a percent change and/or an absolute number difference when compared with known flow rates for uninfected patients of a similar medical history, and/or with determined (e.g. detected and calculated) flow rates for the same patient prior to infection and/or at earlier stages of infection. Such changes may be analyzed to determine statistical significance, and/or to have at least a certain absolute amount of change. Such determinations of differences are known to those of skill in the art.

Malaria infection may cause changes in one or more blood flow characteristics. Although extensive changes have been documented for cerebral (or severe) malaria caused by *P. falciparum* (see, e.g., Chen et al. (2000) Clin. Microbiol. Rev. 13:439-450), a continuum of effects is present for less severe forms of infection. Blood flow changes may result from (among others) increased binding or association of red blood cells to the vascular endothelium (cytoadherence), or to other erythrocytes (resetting). These bindings will eventually lead to the accumulation of parasitized red blood cells in the local post-capillary microvasculature (sequestration) and obstruct the blood flow (partially or completely), limiting the local oxygen supply. Sequestration may occur throughout the body including, but not limited to, the brain and other organs, including the retina.

In addition to changes in binding, parasitized red blood cells also exhibit changes in mechanical properties of the red blood cells such as, but not limited to, decreased membrane flexibility (decreasing the ease of passage of parasitized red blood cells through the microvasculature), creation of special channels or pores (for transport of parasite nutrients), digestion/modification of membrane components, and/or insertion of parasite-derived polypeptides through the membrane (associated with "knobs"). The flexibility of non-parasitized red blood cells is also decreased in infected patients. The decrease in membrane flexibility in parasitized and non-parasitized red blood cells of infected patients is also associated with changes in blood flow & sequestration.

As used herein, the terms "increase" and "decrease" as related to one or more changes in blood cell characteristics, such as but not limited to, sequestration, binding (e.g. vasculature and/or resetting), and/or mechanical changes (e.g. membranes, pores, knobs). Such changes can be up or down (e.g. depending of the stage of malaria infection), and can be measured using methods known to those of skill in the art and/or described herein. In illustrative embodiments, such changes are detected as a percent change and/or an absolute number difference when compared with known blood cell characteristics for uninfected patients of a similar medical history, and/or with determined (e.g. detected and calculated) blood cell characteristics for the same patient prior to infection and/or at earlier stages of infection. Such changes may be analyzed to determine statistical significance, and/or to have at least a certain absolute amount of change. Such determinations of differences are known to those of skill in the art.

In some embodiments, the one or more methods optionally include providing an indication of malarial infection, optionally automatically. In some embodiments, the indication of malarial infection is optionally an optical indication of malarial infection. In some embodiments, the optical indication of malarial infection includes one or more of a visual indication of malarial infection, an acoustic indication (e.g. tonal or voice readout) of malarial infection, or data corresponding to an indication of malarial infection. In illustrative embodiments, such an indicator of malarial infection may be a readout on a display, optionally graphical or digital, optionally on a monitor and/or part of a transmission, optionally computer-readable. Such a readout may indicate the presence or absence of infection, the likelihood of an infection, the level or severity of infection (e.g. % parasitemia or parasites/µl), the type of infection (e.g. species of malaria), and optionally suggested treatment options, among others.

Embodiments include methods for diagnosing malaria, including providing electromagnetic energy to one or more ocular blood vessels of a subject, the electromagnetic energy configured to induce Raman scattering; optionally selectively detecting one or more characteristics of an electromagnetic response associated with provided electromagnetic energy and substantially localized to the one or more ocular blood vessels; optionally tracking one or more indicators of blood flow in the one or more ocular blood vessels at least partially based on detecting one or more characteristics of an electromagnetic response associated with provided electromagnetic energy; and detecting a Raman spectral response for hemozoin associated with the one or more ocular blood vessels, wherein detection of hemozoin is diagnostic for malaria infection.

As used herein, the term "subject" may include, but is not limited to, one or more living entities including, but not limited to, animals, mammals, humans, reptiles, birds, amphibians, and/or fish. The animals may include, but are not limited to, domesticated, wild, research, zoo, sports, pet, primate, marine, and/or farm animals. Animals include, but are not limited to, bovine, porcine, swine, ovine, murine, canine, avian, feline, equine, and/or rodent animals. Domesticated and/or farm animals include, but are not limited to, chickens, horses, cattle, pigs, sheep, donkeys, mules, rabbits, goats, ducks, geese, chickens, and/or turkeys. Wild animals include, but are not limited to, non-human primates, bear, deer, elk, raccoons, squirrels, wolves, coyotes, opossums, foxes, skunks, and/or cougars. Research animals include, but are not limited to, rats, mice, hamsters, guinea pigs, rabbits, pigs, dogs, cats and/or non-human primates. Pets include, but are not limited to, dogs, cats, gerbils, hamsters, guinea pigs and/or rabbits. Reptiles include, but are not limited to, snakes, lizards, alligators, crocodiles, iguanas, and/or turtles. Avian animals include, but are not limited to, chickens, ducks, geese, owls, sea gulls, eagles, hawks, and/or falcons. Fish include, but are not limited to, farm-raised, wild, pelagic, coastal, sport, commercial, fresh water, salt water, and/or tropical. Marine animals include, but are not limited to, whales, sharks, seals, sea lions, walruses, penguins, dolphins, and/or fish.

Diagnostic methods may be administered by medical professionals (e.g. doctors, nurses, and other trained medical professionals as appropriate), or ultimately any persons empowered to perform such tests and having the requisite knowledge and understanding to perform such tests. The results may be immediately available, and/or require some analysis either by a trained professional, or computer-mediated, for example.

EXAMPLES

The following Examples are provided to illustrate, not to limit, aspects of the present invention. Materials, reagents, devices, and apparatus described in the Examples are commercially available unless otherwise specified.

Example 1

Hemozoin Characterization in Malaria-Infected Red Blood Cells

The intraerythrocytic malaria parasite (e.g. trophozoite of *Plasmodium* spp.) uses hemoglobin as a major nutrient source. Digestion of hemoglobin releases heme, which the parasite converts into a virtually insoluble microcrystalline material called hemozoin or malaria pigment. Hemozoin exists at high concentrations within the food vacuole of the malaria-infected red blood cell.

Hemozoin is purified from *Plasmodium* spp. and characterized by methods known in the art including, but not limited to, Fourier transform infrared spectra, electron paramagnetic resonance, Mossbauer spectroscopy, and X-ray absorption spectroscopy (see e.g., Slater et al. (1991) PNAS 88:325-329). Hemozoin consists of heme moieties linked by an iron-carboxylate bond. Hemozoin is spectroscopically identical to the synthetic analogue β-hematin (Fe(III)-protoporphyrin-IX)$_x$.

Hemozoin within the food vacuole of trophozoite-infected functional red blood cells is imaged using Raman spectra at excitation wavelengths of, for example, 488, 514, 568, 633 and 780 nm. An enhancement from hemozoin of $v_4$ (1374 cm$^{-1}$) at 780 nm, together with a poor enhancement of hemoglobin at 780 nm, facilitates Raman imaging of hemozoin within the trophozoite (Wood et al. (2003) FEBS Lett. 554: 247-252).

Raman spectra of normal and malaria-infected red blood cells can be recorded on a Renishaw system 2000 using a 632.8 n excitation line from a helium-neon laser, and a 780 nm excitation line generated by a diode laser, for example. The system can include a modified BH2-UMA Olympus optical microscope and a Zeiss X60 water immersion objective. Spectra can also be generated using, for example, 488 nm and 514 nm excitation lines generated by a Spectra Physics AR$^+$ Stabilite 2017 laser system, and/or 568 nm excitation lines generated by a KR$^+$ Beamlock 2060 laser, both lasers optionally coupled to a Renishaw Raman 200 spectrometer and interfaced to a Leica Raman microscope using a water immersion objective.

Power at the samples is, for example, approximately 2 mW for a 1-2 µm laser spot size. Spectra are recorded over 10 seconds between 1800 and 200 cm$^{-1}$ with a resolution of approximately 1-2 cm$^{-1}$.

Raman images of malaria-infected erythrocytes are generated at the late trophozoite stage using a 780 nm diode laser with a 120 s laser exposure time. The cell does not lyse during this exposure due to the long excitation wavelength and defocused laser beam.

An image is collected by calibrating the position of $v_4$ (1374 cm$^{-1}$) by recording a filter spectrum of hemozoin over an 1800-200 cm$^{-1}$ range. Images are recorded by defocusing the laser approximately 15% to encapsulate the cell, and the scattered light is transmitted through a polarizer. A background image is also recorded at 1800 cm$^{-1}$, well away from all other bands, and subtracted from the $v_4$ image. This minimizes the effects of fluorescence, and removes inconsistencies within the laser spot.

Example 2

Method for Hemozoin Identification in Situ

*Plasmodium* spp. may be detected in situ by spectroscopic identification of hemozoin in the far IR spectrum. IR detection of hemozoin within retinal blood vessels can be made via Raman spectroscopy using high resolution retinal illumination and spectral systems such as those described herein.

In one embodiment, spectroscopic identification of hemozoin in the IR region indicates the presence of *Plasmodium* spp. infection. IR detection of hemozoin within retinal blood vessels can be made via Raman spectroscopy. In-vivo detection can be performed by use of high resolution retinal illumination and imaging systems. A confocal Raman spectroscopic microscope has been demonstrated for in-vivo imaging (Caspers et al. 2003. Biophysical Journal 85:572-580). In vivo confocal Raman spectroscopy provides detailed information about the molecular conformation of tissue, including depth-resolved information. A confocal Raman system may include, for example, a tunable titanium-sapphire laser (model 3900S, Spectra-Physics, Mountain View, Calif.) pumped by an Argon-ion laser (model 2020, Spectra-Physics). Spectra may be recorded using an F/2.1 spectrograph with 6 cm$^{-1}$ spectral resolution and a liquid nitrogen cooled, deep depletion charge-coupled device (CCD) camera with a chip size of 1024×256 pixels (Princeton Instruments, Trenton, N.J.). A 30× numerical aperture (NA) 0.90 water immersion microscope objective with coverglass correction (Lomo, Vermont Optics, Charlotte, Vt.) may be used to focus the laser light from the Raman laser. The objective may be mounted in a fast and accurate piezoelectric focusing drive, accurate to less than 0.1 µm operating in closed loop (position-controlled) mode (Physik Instruments, Walbronn, Germany).

In one approach to capturing a signal for Raman spectroscopic processing, the interaction volume is minimized for local detection. One skilled in the art will recognize that local detection is one approach to achieving signal to noise rations by isolating a volume and/or inhibiting scattered light. One approach to imaging with an effective high lateral confinement uses a scanning laser ophthalmoscope, such as an Adaptive Optics Scanning Laser Ophthalmoscope (AOSLO) for use in retinal imaging (see, e.g., Romero-Borja et al., 2005. Applied Optics 44:4032-4040).

The AOSLO is a merging of adaptive optics (AO) used to correct optical aberrations in the eye, and an SLO. The instrument optionally includes, but is not limited to, a light delivery system, wave-front sensing, wave-front compensation, raster scanning, light detection, and frame grabbing. In the light delivery system, light from a laser diode of a selected wavelength(s) is coupled to the instrument optionally by way of a single mode optical fiber whose output end provides a point source of light. The single scanning light source is optionally used for both imaging and for wave-front sensing. Wave-front sensing is optionally accomplished using a Shack-Hartmann sensor with a square lenslet array and a digital CCD camera. Wave-front compensation is optionally achieved using a 37-channel deformable mirror (DM) conjugate to the entrance pupil of the eye. The DM is shaped to correct the wave-front of the light on its path to the eye, as well as the wave-front of the light on its return path toward the confocal pinhole at the detection (imaging) arm. A resonant and galvanometric (raster) scanner combination is optionally used to scan the laser beam onto the retina to provide illumination. Diffusely reflected light from the focused spot on the retina is refocused onto the confocal pinhole and optionally detected by a GaAs photomultiplier tube (PMT). A Matrox Genesis frame grabber is optionally used to perform digital image reconstruction from the PMT signal.

The AOSLO optionally incorporates retinal tracking features (TAOSLO) or other tracking or adaptive imaging processes that are able to optionally increase the effective imaging time (see, e.g., Hammer et al. (2006) Optics Express 14:3354-3367). The TAOSLO optionally includes, but is not limited to, a retinal tracker with a wide-field line-scanning laser ophthalmoscope (T-LSLO or TSLO) to stabilize to fixed and repeatable retinal coordinates and correct for the adverse effects of eye motion, a flying spot scanning laser ophthalmoscope (SLO) that produces high magnification confocal images, and an adaptive optics (AO) component that senses wave-front distortion and corrects ocular aberrations. Control of hardware and acquisition and processing of images and data from the sub-systems is optionally accomplished from a single software platform. Overall, the user has a wide-field view of a large portion of the retina, a high magnification view of a particular region of interest (e.g. blood vessels), and a view of the ocular aberrations optionally in both the raw form of wave-front slopes and the refined form of wave-front error map and Zernike coefficient plot.

In one approach, a selected effective volume of fluid, such as blood, may be tracked through a process of translating an imaged pixel or voxel according to a predicted or measured velocity of the effective volume. Such translating may be through physical processes, such as adaptive optics or dynamic orientation of an optical system or may be done computationally in a processing system by correlating data corresponding to pixels or voxels with successive locations in successive frames. Such tracking can permit detection using information from two or more periods, and in some cases, many more than two periods, to increase the effective imaging time. Such increased effective imaging time can provide increased signal to noise ratio, according to known techniques (such as signal integration) for processing a plurality of signals or signals over extended intervals. In addition, other approaches to increasing signal to noise ratios or for tomographic imaging, such as optical coherence tomography (OCT) may be implemented with retinal imaging (see, e.g., Zhang et al. (2005) Optics Express 13:4792-4811). OCT is an interferometric imaging approach that provides very high sensitivity and axial resolution.

Enhancing Raman scattering cross-section can increase energy returned to a detector. Such approaches can increase signal to noise ratios in some configurations and/or may reduce imaging time (or sampling interval) for a given pixel or voxel. For in vivo retinal imaging, this enhancement can be achieved by methods such as resonant Raman scattering, or non-linear Raman scattering. In one embodiment, Coherent Anti-Stokes Raman Scattering (CARS) microscopy can employ a four-wave mixing process, having a quadratic dependence on the incident laser power according to a technique described by, for example, Cheng & Xie (2004) Journal of Physical Chemistry B 108:827-840. In some configurations, picosecond and/or sub-picosecond pulses can reduce imaging time (or sampling intervals), while reducing incident fluence.

In one approach, an imager may be implemented as a fixed-base instrument, to which the patient is brought for examination. It is alternatively envisioned to use a portable, e.g., handheld, instrument, which may incorporate several differences from a fixed instrument. One is the use of smaller, or more compactly packaged, optical components. Such reduced-size instruments are known, including for instance, a handheld Raman Microspectrometer (see, e.g., Lieber & Mahadevan-Jansen (2007) Optics Express 15:11874-11882), and a miniature Fourier Transform Raman Spectrometer developed for use in robotic spacecraft (Tools for Robotic In-situ Optical Microscopy and Raman Spectroscopy on Mars).

Another useful feature in a mobile and/or handheld module is a motion compensation system, in which the image is held fixed relative to a horizon (or other reference) or to aspects of the user, such as the user's retina, despite relative motion of the device and the user. Such motion compensation can be achieved through a variety of approaches. For example, a variety of approaches are available for tracking one or more image features, by measuring device motion and making compensatory adjustments to the optical path, by defining reference frames through approaches such as gyroscopic devices, or by combinations of such techniques. While some of the previously described approaches incorporate illumination sources, such as laser diodes or LEDs, that may be represented as directly coupled to optical systems (e.g., as shown from the SLO system), in some approaches, the illumination source may be separately mounted or carried. In one such approach, an optical fiber is coupled intermediate the illuminating source and additional portions of the system, such as optical components. In another approach, laser light can be delivered to other components of the system by free-space transmission.

Example 3

Device for Hemozoin Identification in Situ

A variety of devices known in the art and/or described herein may be used to detect hemozoin in situ combined with spectroscopic localization and/or tracking in the ocular blood vessels. A variety of apparatus and/or devices are presented herein, and it is intended and envisioned that the components of these apparatus and/or devices, in whole or in part, may be combined, interchanged, and/or substituted as appropriate to perform one or more of the methods disclosed herein. In some embodiments, one or more apparatus and/or devices may include one or more system implementations including operations, and/or include one or more computing devices and/or systems configured to perform one or more methods.

FIG. 1 depicts an illustrative embodiment of a system that may be used for detection of hemozoin and/or for malaria diagnosis in retinal blood vessels. The optical system 1000 depicted in FIG. 1 optionally includes one or more of one or more scanning/projection system 100 (e.g. including one or more electromagnetic energy source), one or more beam splitter 200, one or more optical system 300, one or more detection subsystems 400 (e.g. one or more detectors), and/or one or more system electronics 500 (e.g. one or ore controllers).

In illustrative embodiments, electromagnetic energy 110 (e.g. illumination and/or illuminating beams) emitted from the scanning/projection system 100 (e.g. electromagnetic energy source) passes through the beam splitter 200 and the optional optical system 300 (e.g. lens, optical train) before entering the eye 2000 through the pupil and contacting the back of the eye (e.g. fovea or retina 2100). A portion of the electromagnetic energy that is reflected and/or scattered 130 (e.g. Raman backscatter) exits the eye 2000 through the pupil optionally passing back through an optical system 300 to the beam splitter 200 where the energy is optionally re-directed 140 to a detection subsystem 400 (e.g. one or more detectors for image capture, spectral detection, among others). System electronics 500 (e.g. one or more controllers, optionally processors, computers, wireless, hardwired, among others) deconvolve and/or process the detected spectra, and/or provide output indicating one or more of presence, absence, level and/or location of detection of hemozoin, among other parameters. The system electronics 500 optionally control the illumination, as well as the scanning parameters, provided by the scanning/projection system 100, and optionally control the image/spectra capture parameters for the detection subsystem 400.

Returning to FIG. 1, an optical system 1000 includes a scanning/projection system 100 and a detection subsystem 400 each operating under control of system electronics 500. The scanning/projection system 100 may be implemented in a variety of formats, such as, but not limited to, an optical scanner-based system, such as that described in one or more of U.S. Pat. No. 6,445,362, U.S. 2006/0284790 and/or U.S. 2005/0020926.

In one approach, the scanning/projection system 100 directs one or more illuminating beams of light 110 through a beam splitter 200 and through an optical system 300 toward a subject's eye 2000. In an illustrative embodiment, the scanning/projection system 100 employs a conventional light source, such as a laser diode or fiber coupled laser at an input wavelength of 830 nm, for at least one of the illuminating beams 110. The scanning/projection system 100 scans the illuminating beams 110 through a raster pattern or a Lissajous pattern, for example.

The optical system 300 couples the scanned illuminating beam 110 into the eye, through its pupil where the illuminating beam of light 110 strikes the retina 2100. In some approaches, the optical system may provide a beam 120 that converges in a field of interest, such as at or near the surface of a retina 2100. In other approaches, the beam may be substantially collimated.

The beam splitter 200 may be any of a variety of optical structures that can selectively transmit and/or re-direct at least a portion of light along one or more paths. In an illustrative embodiment, the beam splitter may be responsive to one or more wavelengths of light to selectively transmit and/or re-direct at least a portion of light. As will be described herein, some of the light that returns from the field of interest may be wavelength shifted according to Raman scattering. The beam splitter may be configured to selectively transmit to the eye light at an input wavelength, while selectively redirecting light at a Raman scattered wavelength, and/or the input wavelength. Note that the beam splitter may also redirect all or a portion of the returned light responsive to polarization or other characteristics of light.

Further, although the optical system 300 is represented with a conventional lens symbol for clarity of presentation, the optical system 300 may include a plurality of lenses, and/or a variety of optical components, such as lenses, mirrors, apertures, wavelength filters, polarization filters, chromatic correction devices, diffractive components or other components. Moreover, the optical system 300 may include components positioned intermediate to the scanning/projection system and to the beam splitter or intermediate to the beam splitter and to the detection subsystem.

As represented by the ray 130, a portion of the light in the beam 120 returns from the field of interest (e.g. retina 2100), through the optical system 300 to the beam splitter 200, where at least a portion of the light that returns is redirected 140 toward the detection subsystem 400. The detection subsystem 400 receives the redirected light and provides a corresponding signal to the system electronics 500.

For a common input and output wavelength, the input intensity, scanning frequency, optical train, scanning profile, timing and control circuitry, and other aspects of selectively identifying the amount of light energy returned from each location on a user's retina 2100 may be implemented in a variety of fashions, such as those implemented for scanning laser ophthalmoscopes or scanning beam endoscopes. The design tools, optics, electronics, scanning systems, and other aspects of such systems may be adapted for operation according to the embodiments herein. For example, one or more of the input beams 120 may be utilized for capturing an image of the retina, or features of the eye such as vasculature according to known techniques such as those of scanning laser ophthalmoscopes. In such a configuration, the scanning/projection system may include a light source at wavelength different from 830 nm, such as a visible or infrared wavelength, for illumination in addition to the one or more input beams 120 at a wavelength, such as 830 nm, selected to induce Raman scattering. Alternatively, the scanning/projection system may use a single wavelength of light for both image capture and for inducing Raman-shifted wavelengths.

As described above, the beam splitter may utilize wavelength differences between input and return optical energy as one aspect of selectively directing return optical energy to the detection subsystem 400.

Figure 2:
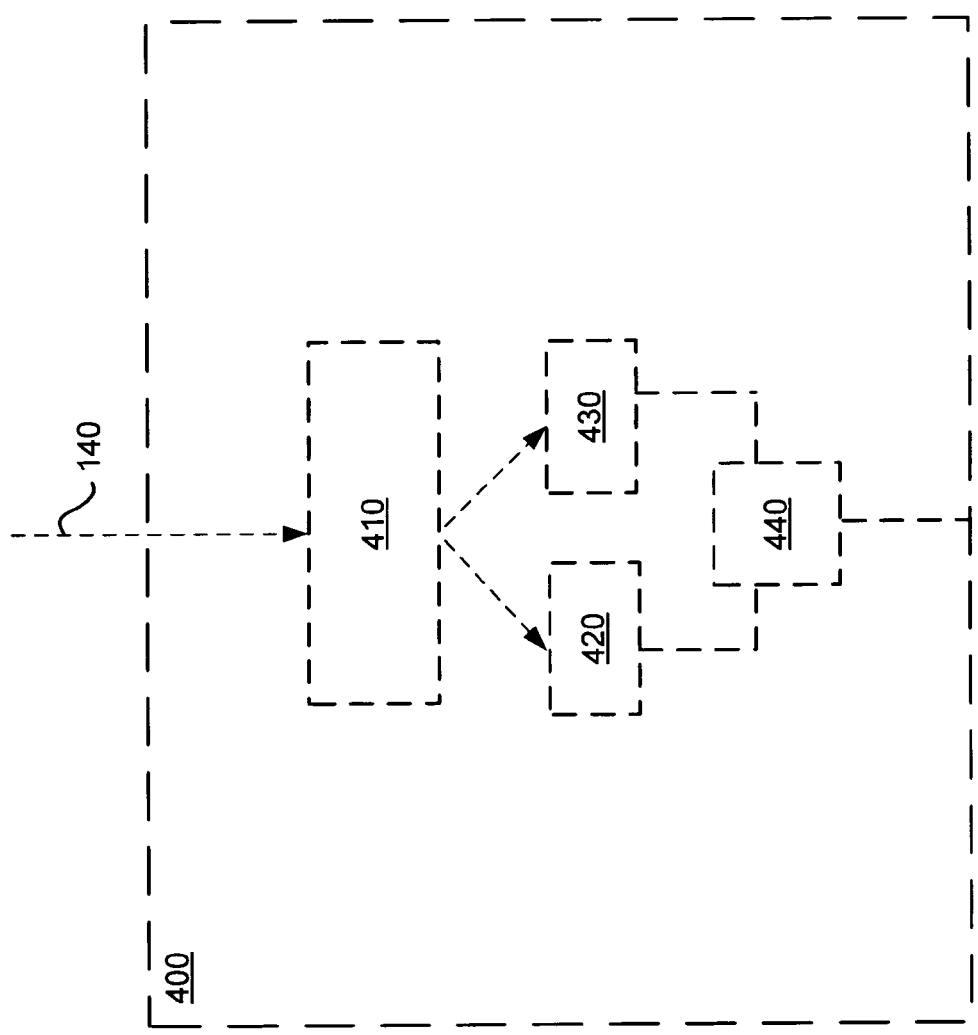
FIG. 2 is a schematic of an optional embodiment of the detector subsystem of the spectral imaging and/or optical system.

As shown diagrammatically in FIG. 2, the detection subsystem 400 may be configured for operation at a Raman-scattered return wavelength as well as at an imaging wavelength. In this approach, a spectral separator 410, such as a wavelength division demultiplexer, diffractive element, or similar device separates returned light 140 entering the detection subsystem 400 into spectral components. A first of the spectral components corresponds to a Raman-scattered return wavelength and is directed toward a first detector 420. A second of the spectral components corresponds to the imaging wavelength and is directed toward a second detector 430.

While the representation in FIG. 2 shows two detectors 420 and 430, in some embodiments one detector may perform both (or all) detection functions, while in other embodiments, multiple detectors may optionally be used to collect a variety of spectral and/or image components as discussed herein.

While the representation in FIG. 2 shows the spectral separator 410 splitting the returned light into two spectral components, in some approaches more than two spectral components may be used. For example, the spectral separator 410 may be configured to provide to spatially separated components at two or more Raman-scattered return wavelengths to two different detectors. Additionally, or alternatively, the spectral separator 410 may be configured to provide two spatially separated components at two or more imaging wavelengths. For example, red, green, and blue wavelengths may be utilized to provide color information.

Spectral and/or image information collected by one or more of the detectors 420 and/or 430 is provided to control circuitry 440 (or optionally directly to system electronics 500) for additional analysis. Analysis may include, but is not limited to, mapping vasculature locations, tracking blood flow, identifying spectral signatures and/or images of interest (e.g. hemozoin-specific Raman shifts, malaria-related changes in blood flow, malaria-related characteristics of red blood cells, among others). Control circuitry may be programmable, may perform the analysis automatically, and may be remotely, manually, directly, and/or feedback controlled. For example, detection of hemozoin-related spectra may result in additional data analysis (e.g. assessment of other malaria-related indicators such as sequestration and/or binding), flagged readouts to system monitors (e.g. positive hemozoin detection and detection level), and/or additional imaging/spectra collection (e.g. prompts for longer collection times, or collection at alternate parameters/locations). Information transfer may be digitized or analog, and may include wireless transmissions.

In addition to the spectral separator 410, the optical system 300 may be configured to accommodate differences in response of the eye lens for input wavelengths that may be different than typical scanning laser ophthalmoscopes. Design of such systems may be implemented according to known design techniques, such as computer-based optical modeling. One skilled in the art will recognize that the scanning/projection system 100 and optical system 300 may be implemented as a confocal system or a non-confocal scanning beam system, such as those found in some ophthalmoscopes and some scanning beam imagers.

While the portion of the light that returns from the field of interest is represented as the ray 130 in FIG. 1, one skilled in the art will recognize that another portion of the light may be scattered or absorbed, such that the portion of the light that returns from the field of interest is typically substantially less than all of the light in the beam 110/120. Moreover, some of the light that returns from the field of interest may not enter or be accepted by the optical system 300. In many cases, the amount of light that enters and is accepted by the optical system 300 will be a function of an entrance aperture of the optical system 300 and a numerical aperture of the optical system 300, which typically define the area and angle, respectively, at which an optical system receives and accepts light.

Accordingly, the amount of light energy that arrives at the detection subsystem 400 is typically a very small portion of the overall amount of optical energy entering the eye 2000. Moreover, the amount of optical energy entering the eye 2000 is often limited according to conventional safety metrics, such as laser safety regulations.

In an illustrative embodiment, where the light source is an 830 nm source, the illuminating beam of light 110 has an energy of 0.36 microjoules in a sampling interval, for example of 1 ns, giving approximately $1.5 \times 10^{12}$ photons. For an eye transmission of 75%, approximately $1.1 \times 10^{12}$ photons strike the retina. Assuming a spot size of 5 μm on the retina, which corresponds roughly to the size of a red blood cell, approximately 9% of the photons (or approximately $1.0 \times 10^{11}$ photons) in the illuminating beam of light 110 strike hemozoin (corresponding to a 1.5 micron hemozoin-loaded parasite).

For a typical Raman scattering efficiency of about $10^{-8}$, this provides approximately $1.0 \times 10^{3}$ photons per sampling interval. Because 830 nm can excite a resonance, the Raman scattering efficiency may be increased by a factor of approximately 100, providing approximately $10^{5}$ photons that are Raman scattered in a sampling interval. A significant portion (approximately 10%) of the scattered photons are at a targeted feature in the Raman spectra (e.g., the resonantly enhanced 1374 $cm^{-1}$ peak), yielding $10^{4}$ photons. Since only a fraction of the scattered photons escape through the eye pupil, (e.g., transmission of 40% and angular fraction of 1%), this produces approximately 40 photons per sampling interval. For a 25% efficient detection system, on the order of 10 photons reach an actual photo detector within the sampling interval. Ignoring for the moment optical noise, such amounts of photons may be detected by cooled detectors, photomultiplier tubes, or similar approaches.

In some configurations, the illuminating beams of light 110 may induce fluorescence in, or around the retina 2100. A portion of the light emitted as a result of fluorescence may be emitted along a path that would lead to the detector subsystem 400, and can be considered a form of optical noise. Use of IR or NIR illumination, rather than visible or UV, for inducing the Raman scattering will result in substantial reductions of fluorescence. A large portion of occurring fluorescence will typically be in a spectral band different from Raman-induced scattering. Consequently, a large portion of such light may be removed through simple filtering. Additionally, fluorescence emission typically involves a delay relative to direct scattering. Thus, such fluorescent emissions may be reduced by time-gating. That is, the illuminating beams of light 110 can be constructed with short pulses of light. The detector subsystem 400 can be activated and deactivated synchronously with the short pulses of light so that the detector subsystem 400 captures primarily reflected light without capturing light from induced fluorescence.

According to substantially the same arrangement as represented in FIGS. 1 and 2, an optical system may implement Coherent Anti-Stokes Raman Spectroscopy (CARS). CARS has been described in greater detail in, for example, "Chemical imaging of tissue in vivo with video-rate coherent anti-Stokes Raman scattering microscopy" (Evans, et. al. (2005) PNAS 102:16807-16812). In one such approach, the illuminating beams of light 110 employ near infrared radiation, for example at 1060 nm and 925 nm in order to coherently excite anti-stokes Raman scattering at, for example, 1374 $cm^{-1}$.

Such CARS systems can employ fluences on the order of $7\text{-}10^{-7}$ J, corresponding to $3.5 \times 10^{12}$ photons per sampling interval. Due to lower incident transmission, the number of photons reaching the retina is only slightly higher than described above, approximately $1.4 \times 10^{11}$ photons. However, CARS can increase basic Raman scattering by approximately 100,000. Following the analysis above relating to the percentage of Raman-scattered photons reaching the detector, the number of photons reaching the detector in a sampling interval is on the order of 10,000.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

For ease of reading, all values described herein, and all numerical ranges described herein are approximate and should be read as including the word "about" or "approximately" prior to each numeral, unless context indicates otherwise. For example, the range "0.0001 to 0.01" is meant to read as "about 0.0001 to about 0.01."

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for identifying hemozoin, comprising:
   inducing a spectral response of one or more retinal ocular blood vessels via a scanning assembly operable to deliver, through a pupil, electromagnetic energy to the one or more retinal ocular blood vessels, the electromagnetic energy configured to induce Raman scattering of hemozoin present within the one or more ocular blood vessels;
   tracking one or more indicators of blood flow in the one or more retinal ocular blood vessels at least partially based on detecting one or more characteristics of the spectral response of the one or more retinal ocular blood vessels;
   detecting a Raman spectral response for hemozoin associated with the one or more retinal ocular blood vessels; and
   generating a response indicative of a malaria-related change in blood flow based on the tracking of the one or more indicators of blood flow in the one or more retinal ocular blood vessels.

2. The method of claim 1, wherein tracking one or more indicators of blood flow in the one or more retinal ocular blood vessels comprises:
   tracking one or more blood cells in the one or more retinal ocular blood vessels.

3. The method of claim 1, wherein tracking one or more indicators of blood flow in the one or more retinal ocular blood vessels comprises:
   tracking one or more indicators of blood flow velocity in the one or more retinal ocular blood vessels.

4. The method of claim 3, wherein tracking one or more indicators of blood flow velocity in the one or more retinal ocular blood vessels comprises:
   tracking the one or more indicators of blood flow velocity using Doppler effect.

5. The method of claim 4, wherein tracking the one or more indicators of blood flow velocity using Doppler effect comprises:
   tracking the one or more indicators of blood flow velocity using Doppler effect generated by ultrasound.

6. The method of claim 4, wherein tracking the one or more indicators of blood flow velocity using Doppler effect comprises:
   tracking the one or more indicators of blood flow velocity using Doppler effect generated by electromagnetic energy.

7. The method of claim 4, wherein tracking the one or more indicators of blood flow velocity using Doppler effect comprises:
   tracking the one or more indicators of blood flow velocity using Doppler effect generated by acoustic energy.

8. The method of claim 1, further comprising:
   automatically processing the detected Raman spectral response.

9. The method of claim 1, further comprising:
   correlating the detected Raman spectral response with malaria infection.

10. The method of claim 1, further comprising:
    automatically providing an indication of malarial infection.

11. The method of claim 1, wherein the electromagnetic energy is delivered at wavelengths of less than about 1.5 µms.

12. The method of claim 1, wherein the electromagnetic energy is delivered at wavelengths of about 0.4 µms to 1.5 µms.

13. The method of claim 1, wherein the electromagnetic energy is delivered in short pulses.

14. The method of claim 13, wherein the short pulses are sub microsecond pulses.

15. The method of claim 1, wherein the electromagnetic energy is delivered at an energy about equal to an electronic energy transition in hemozoin.

16. The method of claim 1, wherein tracking one or more blood cells in the one or more retinal ocular blood vessels is at least partially based on a predicted flow of the one or more blood cells in the one or more retinal ocular blood vessels.

17. The method of claim 1, wherein tracking one or more blood cells in the one or more retinal ocular blood vessels is at least partially based on a detected flow of the one or more blood cells in the one or more retinal ocular blood vessels.

18. The method of claim 1, wherein the electromagnetic energy is delivered to one or more retinal ocular blood vessels at least partially based on a predicted location of the one or more retinal ocular blood vessels.

19. The method of claim 1, wherein the electromagnetic energy is delivered to one or more retinal ocular blood vessels at least partially based on a detected location of the one or more retinal ocular blood vessels.

20. The method of claim 1, further comprising:
analyzing the one or more characteristics of the electromagnetic response associated with electromagnetic energy to determine locations of the one or more retinal ocular blood vessels.

21. The method of claim 1, further comprising:
analyzing the one or more characteristics of the electromagnetic response associated with the electromagnetic energy to determine one or more blood flow characteristics of the one or more retinal ocular blood vessels.

22. The method of claim 21, wherein analyzing includes comparing the determined one or more blood flow characteristics with one or more expected blood flow characteristics.

23. The method of claim 22, wherein the expected blood flow characteristics include the expected blood flow characteristics for a non-infected subject.

24. The method of claim 22, wherein the expected blood flow characteristics include the expected blood flow characteristics for an infected subject.

25. The method of claim 21, wherein analyzing includes comparing the determined one or more blood flow characteristics with one or more predicted blood flow characteristics.

26. The method of claim 1, wherein detecting a Raman spectral response for hemozoin comprises:
analyzing the Raman spectral response for hemozoin for selected spectra, wherein the selected spectra include a hemozoin-specific signature.

27. The method of claim 1, wherein detecting a Raman spectral response for hemozoin comprises:
detecting the Raman spectral response from about 1700 cm−1 through about 1000 cm−1.

28. The method of claim 1, wherein detecting a Raman spectral response for hemozoin comprises:
detecting the Raman spectral response at one or more ranges including about 1620 cm−1 through about 1680 cm−1, about 1200 cm−1 through about 1250 cm−1, or about 1350 cm−1 through about 1400 cm−1.

29. A method for diagnosing malaria, comprising:
inducing a Raman spectral response of one or more retinal ocular blood vessels via a scanning assembly operable to generate an electromagnetic energy scanning beam that enters through a pupil of a subject and illuminates the one or more retinal ocular blood vessels, the scanning beam configured to induce Raman scattering of hemozoin present within the one or more ocular blood vessels;
generating a response indicative of a malarial infection based on the Raman spectral response associated with the one or more retinal ocular blood vessels;
tracking one or more indicators of blood flow in the one or more retinal ocular blood vessels at least partially based on the Raman spectral response; and
generating a response indicative of a malaria-related change in blood flow based on the tracking of the one or more indicators of blood flow in the one or more retinal ocular blood vessels.

30. The method for diagnosing malaria of claim 29, wherein generating the response indicative of a malarial infection includes providing at least one of an acoustic indication of malarial infection, an optical indication of malarial infection, or a visual indication of a malarial infection.

31. The method for diagnosing malaria of claim 29, wherein generating the response indicative of a malarial infection includes providing data corresponding to an indication of a malarial infection.

* * * * *